United States Patent
Mannello et al.

(10) Patent No.: US 11,833,186 B2
(45) Date of Patent: *Dec. 5, 2023

(54) METHODS AND COMPOSITIONS FOR IMPROVING QUALITY OF LIFE AND INCREASING ACTIVITY IN AGING AND CHRONICALLY ILL MAMMALS

(71) Applicant: MYOS CORP., Cedar Knolls, NJ (US)

(72) Inventors: Joseph Mannello, Cedar Knolls, NJ (US); Maghsoud Dariani, Cedar Knolls, NJ (US); Neerav D. Padliya, Cedar Knolls, NJ (US)

(73) Assignee: MYOS CORP., Cedar Knolls, NJ (US)

( * ) Notice: Subject to any disclaimer, the term of this patent is extended or adjusted under 35 U.S.C. 154(b) by 510 days.

This patent is subject to a terminal disclaimer.

(21) Appl. No.: 16/775,908

(22) Filed: Jan. 29, 2020

(65) Prior Publication Data
US 2020/0246422 A1  Aug. 6, 2020

Related U.S. Application Data

(60) Provisional application No. 62/800,014, filed on Feb. 1, 2019.

(51) Int. Cl.
*A61K 38/17* (2006.01)
*A61P 21/00* (2006.01)
*A61K 35/57* (2015.01)

(52) U.S. Cl.
CPC .......... *A61K 38/1703* (2013.01); *A61K 35/57* (2013.01); *A61P 21/00* (2018.01)

(58) Field of Classification Search
CPC .................................. A61K 35/57; A61P 21/00
See application file for complete search history.

(56) References Cited

U.S. PATENT DOCUMENTS

| | | | |
|---|---|---|---|
| 8,815,320 B2 * | 8/2014 | Buxmann | A23L 5/30 514/774 |
| 2003/0162715 A1 * | 8/2003 | Duan | C07K 14/4703 514/9.9 |
| 2007/0275036 A1 | 11/2007 | Green, III et al. | 424/439 |
| 2018/0021388 A1 * | 1/2018 | Green, III | A61K 35/57 424/581 |

FOREIGN PATENT DOCUMENTS

| | | |
|---|---|---|
| WO | 2017/009004 | 1/2017 |
| WO | 2020/046466 | 3/2020 |

OTHER PUBLICATIONS

Freeman et al. "Polyradiculoneuritis in Dogs, Acute" Saunders, 1pg 2011 (Year: 2011).*
Lisa Desatnik "Canine Hip Dysplasia Exercises | So Much PETential" Dec. 23, 2015, 5 pgs (Year: 2015).*
Power Thesaurus "so that synonyms" 1 pg accessed Mar. 25, 2023 (Year: 2023).*
Britt et al. "In a Randomized, Placebo-Controlled Cross-Over Study, Administration of 6 and 12G Fortetropin® Does Not Reduce Serum Myostatin in Healthy Adult Dogs Over 72-Hours" Front. Vet. Sci, 8:680576, 8pgs, article (Year: 2021).*
Hetrick et al. "Evaluation of Fortetropin in geriatric and senior dogs with reduced mobility" Can Vet J 2022;63;1057-1060, article (Year: 2022).*
Rodino-Klapac et al. "Inhibition of Myostatin With Emphasis on Follistatin as a Therapy for Muscle Disease" Muscle Nerve. Mar. 2009 ; 39(3): 283-296 (Year: 2009).*
Tsuchida "Myostatin inhibition by a follistatin-derived peptide ameliorates the pathophysiology of muscular dystrophy model mice" Acta Myologica • 2008; XXVII; p. 14-18 (Year: 2008).*
International Preliminary Report on Patentability in PCT/US2020/015628 dated Aug. 12, 2021.
International Search Report and Written Opinion in PCT/US2020/15628 dated May 28, 2020.
Ashton et al. "The Effects of a Natural Myostatin Inhibitor Derived from Fertilized Egg Yolk on Serum Myostatin Level and Lean Muscle Thickness and Mass: A Randomized Double Blind, Placebo-Controlled Trial" The Journal of Frailty and Aging 2015 p. 74.
Sharp et al. "The Effects of Fortetropin Supplementation on Body Composition, strength, and Power in Humans and Mechanism of Action in a Rodent Model" Journal of the American College of Nutrition 2016 pp. 1-13.
Wilson et al. The Effects of Fertilized Egg Yolk Isolates on Anabolic and Catabolic Signaling in Skeletal Muscle FASEB 2015 p. 819.1.

* cited by examiner

*Primary Examiner* — Thane Underdahl
(74) *Attorney, Agent, or Firm* — LICATA & TYRRELL P.C.

(57) ABSTRACT

Methods for improving quality of life and/or increasing activity in an aging and/or chronically ill mammal via administration of a composition of egg powder protein are provided.

7 Claims, No Drawings

METHODS AND COMPOSITIONS FOR IMPROVING QUALITY OF LIFE AND INCREASING ACTIVITY IN AGING AND CHRONICALLY ILL MAMMALS

This patent application claims the benefit of priority from U.S. Provisional Application Ser. No. 62/800,014 filed Feb. 1, 2019, teachings of which are incorporated herein by reference in their entirety.

BACKGROUND

While aging in mammals may vary, typically advanced years often bring changes in the ability to move about easily. Further, aging mammals often exhibit muscle loss, weakness and decreased energy. Similar effects can be observed in mammals suffering from chronic illnesses. These changes can negatively affect both quality of life and activity of the aging mammal.

Supplements that include glucosamine, green-lipped mussel, chondroitin and omega-3 fatty acids have been suggested to support the structure and function of joints in dogs as they age inclusive of maintaining healthy cartilage and connective tissue as well as helping to relieve occasional joint stiffness and discomfort from daily activity. See https:// with the extension petbasics.com/dog-education/senior-dog-care-supplements/ of of the world wide web.

Supplementing with long-chain polyunsaturated omega-3 fatty acids like eicosapentaenoic acid (EPA) and docosahexaenoic acid (DHA) have also been suggested for older dogs with arthritis or cognition problems. See https:// with the extension akc.org/expert-advice/nutrition/nutrition-and-supplements-for-senior-dogs/ of of the world wide web.

There is a need for compositions and methods of alleviating more of the negative effects on quality of life and activity in aging and/or chronically ill mammals.

SUMMARY

The present invention relates to a method for improving quality of life and/or increasing activity in an aging mammal and/or chronically ill mammal via administration of a composition comprising egg yolk powder to the mammal.

In one nonlimiting embodiment, quality of life is improved in the mammal by alleviation and/or inhibition of negative, age-related or illness-related effects on quality of life and/or activity in the mammal.

In one nonlimiting embodiment, the composition administered is FORTETROPIN.

The present invention also relates to compositions comprising egg yolk powder for use in methods of improving quality of life and/or increasing activity in an aging mammal and/or chronically ill mammal.

DETAILED DESCRIPTION

The present invention provides methods and compositions for improving quality of life and/or increasing activity in an aging and/or chronically ill mammal.

Compositions administered in accordance with the present invention comprise egg yolk powder or one or more proteins and/or lipids derived from egg yolk which are effective in improving quality of life and/or increasing activity in an aging mammal.

In one nonlimiting embodiment, the composition administered is FORTETROPIN. FORTETROPIN is a fertilized egg yolk derived product used as a dietary and nutritional supplement (MYOS RENS TECHNOLOGY INC., Cedar Knolls, NJ). A method for production of FORTETROPIN is disclosed in U.S. Pat. No. 8,815,320, teachings of which are herein incorporated by reference in their entirety.

In another nonlimiting embodiment, the composition comprises an avian follistatin such as described in U.S. Published Patent Application No. 2007/0275036, the disclosure of which is incorporated herein by reference in its entirety and/or other proteins and/or lipids found in avian eggs and which are beneficial in growth and development of lean muscle tissue.

In another embodiment, the composition comprises a spray dried egg yolk powder or one or more proteins and/or lipids derived from egg yolk such as described in U.S. patent application Ser. No. 16/151,601, the disclosure of which is incorporated herein by reference in its entirety.

Disclosed herein are methods for use of compositions comprising egg yolk powder in the alleviation and/or inhibition of negative, age-related effects on quality of life and/or activity in mammals. In these methods, the composition is administered to an aging mammal in an amount effective to alleviate one or more negative, age-related effects on quality of life and/or activity in the mammal.

By "mammals" it is meant to include, but is not limited to, humans, apes, monkeys, cows, horses, sheep, goats, dogs, cats, mice, rats, and transgenic species thereof.

In one nonlimiting embodiment, the mammal is a dog.

In one nonlimiting embodiment, the mammal is a human.

By "negative, effects on quality of life and/or activity" resulting from aging or chronic illness it is meant to include, but is not limited to, muscle loss, weakness, stiffness, decreased energy and/or decreased mobility.

In one nonlimiting embodiment, the negative effects result from long-term oral corticosteroid administration.

In one nonlimiting embodiment, the negative effects result from a chronic disease associated with lean body mass wasting. Nonlimiting examples include kidney disease, liver disease, cancer, cardiac disease, cachexia, HIV/AIDS, amyotrophic lateral sclerosis (ALS), dermatomyositis, Guillian-Barr syndrome, multiple sclerosis, muscular dystrophy, neuropathy, osteoarthritis, polio, polymyositis, rheumatoid arthritis, spinal muscular atrophy, In one nonlimiting embodiment, wherein the mammal is a dog, the negative effects result from hip dysplasia or arthritis.

In one nonlimiting embodiment wherein the mammal is a dog, the negative effects result from a chronic infectious disease associated with muscle loss such as, but not limited to, hepatozoonosis or leishmaniasis.

In another nonlimiting embodiment wherein the mammal is a dog, the negative, age-related effects results from a polyneuropathy such as, but not limited to, Coonhound paralysis, idiopathic polyradiculoneuritis or chronic inflammatory demyelinating polyneuropathy.

By "alleviation and/or inhibition of negative effects on quality of life and/or activity in mammals" for purposes of this invention, it is meant to include, but is not limited to, reduced muscle loss, reduced weakness, reduced stiffness, increased strength, increased energy and/or increased mobility in the mammal after administration of the composition as compared to prior to administration.

In one nonlimiting embodiment, the egg yolk powder composition administered is FORTETROPIN produced in accordance with the process described in U.S. Pat. No. 8,815,320.

In one nonlimiting embodiment, production of an egg yolk powder compositions such as, but not limited to, FORTETROPIN is optimized to enhance potency as it relates to alleviating and/or inhibiting negative effects on quality of life and/or activity in aging or chronically ill mammals by modifying one or more egg yolk-related parameters such as, but not limited to, incubation time post-lay, fertility status and breed of chicken.

In one nonlimiting embodiment, the composition comprising egg yolk powder is administered orally on a daily basis, one, two or three times a day.

In one nonlimiting embodiment, the egg yolk powder composition is administered orally on a daily basis in an amount ranging from about 3 to about 25 grams/day, about 6.6 to about 19.8 grams/day or about 40 to about 300 mg/kg/day, about 80 to about 250 mg/kg/day in humans. In canines, an egg yolk powder composition such as FORTETROPIN is administered orally on a daily basis in an amount ranging from about 200-1000 mg/kg/day or about 300 to about 900 mg/kg/day.

In some embodiments, the composition comprising egg yolk powder is administered at 300 mg/kg daily (one scoop (6600 mg)/22 kg), or the like or a suitable dosage for the weight and characteristics of the mammal. Dosages may be modified for efficacy, for example, may be administered at a higher or lower dosage or administered more than once daily or less than once daily. Mammals may be dosed to the closest ¼ scoop, or the like, without underdosing. The composition may be formed in a powder that may be mixed with other food to facilitate ingestion.

However, as will be understood by the skilled artisan upon reading this disclosure, the compositions described herein can be formulated for administration to a subject via any conventional means including, but not limited to, oral, or buccal.

Moreover, the compositions described herein, can be formulated into any suitable dosage form, including but not limited to, aqueous oral dispersions, liquids, gels, syrups, elixirs, slurries, suspensions and the like, for oral ingestion by an individual in need, solid oral dosage forms, controlled release formulations, fast melt formulations, effervescent formulations, lyophilized formulations, tablets, powders, pills, dragees, capsules, delayed release formulations, aqueous liquid dispersions, self-emulsifying dispersions, solid solutions, liposomal dispersions, solid dosage forms, powders, tablets, capsules, pills, delayed release formulations.

Formulations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including glucose, fructose, lactose, sucrose, mannitol, sorbitol, stevia extract, or sucralose; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Formulations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, pellets, granules. In other embodiments, the pharmaceutical formulation is in the form of a powder. In still other embodiments, the pharmaceutical formulation is in the form of a tablet. Additionally, formulations described herein may be administered as a single capsule or in multiple capsule dosage form. In some embodiments, the formulation is administered in two, or three, or four, capsules or tablets.

Soft gel or soft gelatin capsules may be prepared, for example, without limitation, by dispersing the formulation in an appropriate vehicle (vegetable oils are commonly used) to form a high viscosity mixture. This mixture is then encapsulated with a gelatin-based film using technology and machinery known to those in the soft gel industry. The industrial units so formed are then dried to constant weight.

In some embodiments, the formulations may include other medicinal or pharmaceutical agents, carriers, diluents, dispersing agents, suspending agents, thickening agents, adjuvants, such as preserving, stabilizing, wetting or emulsifying agents, solution promoters, and/or buffers. In addition, the formulations can also contain other therapeutically valuable substances.

The formulations described herein can include egg yolk powder and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination (s) thereof. In still other aspects, using standard coating procedures, a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Formulations including egg yolk powder, as described herein, may be manufactured in a conventional manner, such as, by way of example only, by means of conventional mixing, dissolving, granulating, dragee-making, levigating, emulsifying, encapsulating, entrapping or compression processes.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Binders imparting cohesive qualities may also be used. Examples include, but are not limited to, alginic acid and salts thereof; cellulose derivatives such as carboxymethylcellulose, methylcellulose, hydroxypropylmethylcellulose, hydroxyethylcellulose, hydroxypropylcellulose, ethylcellulose, and microcrystalline cellulose; microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose, glucose, dextrose, molasses, mannitol, sorbitol, xylitol, and lactose; a natural or synthetic gum such as acacia, tragacanth, ghatti gum, mucilage of isapol husks, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder.

Formulators skilled in art can determine the binder level for the formulations, but binder usage level of up to 70% in tablet formulations is common.

Compositions may further comprise carriers of relatively nontoxic chemical compounds or agents that facilitate the incorporation of a compound into cells or tissues. Nonlimiting examples include binders, suspending agents, disintegration agents, filling agents, surfactants, solubilizers, stabilizers, lubricants, wetting agents, diluents, and the like. Suitable carriers for use in solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Dispersing agents and/or viscosity modulating agents include materials that control the diffusion and homogeneity of a compound through liquid media or a granulation method or blend method. In some embodiments, these agents also facilitate the effectiveness of a coating or eroding matrix. Nonlimiting examples of diffusion facilitators/dispersing agents include hydrophilic polymers, electrolytes, a Tween, PEG, polyvinylpyrrolidone, and carbohydrate-based dispersing agents such as hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers, block copolymers of ethylene oxide and propylene oxide; and poloxamines, tetrafunctional block copolymers derived from sequential addition of propylene oxide and ethylene oxide to ethylenediamine, polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents that are particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

Compositions of the present invention may further comprise diluents used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose; dibasic calcium phosphate, dicalcium phosphate dihydrate; tricalcium phosphate, calcium phosphate; anhydrous lactose, spray-dried lactose; pregelatinized starch, compressible sugar; mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; sodium chloride; inositol, bentonite, and the like.

Compositions may further comprise an enteric coating, a substance that remains substantially intact in the stomach but dissolves and releases the egg yolk powder in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

In addition, the compositions may comprise an erosion facilitator, a material that controls the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

Filling agents including compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like can also be included in the compositions. Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In addition, flavoring agents and/or sweeteners can be used in the compositions and may include acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

The compositions may further comprise lubricants and/or glidants that prevent, reduce or inhibit adhesion or friction of materials. Nonlimiting examples of lubricants include stearic acid, calcium hydroxide, talc, sodium stearyl fumerate, a hydrocarbon such as mineral oil, or hydrogenated vegetable oil such as hydrogenated soybean oil, higher fatty acids and their alkali-metal and alkaline earth metal salts, such as aluminum, calcium, magnesium, zinc, stearic acid, sodium stearates, glycerol, talc, waxes, boric acid, sodium benzoate, sodium acetate, sodium chloride, leucine, a polyethylene glycol (e.g., PEG-4000) or a methoxypolyethylene glycol, sodium oleate, sodium benzoate, glyceryl behenate, polyethylene glycol, magnesium or sodium lauryl sulfate, colloidal silica, a starch such as corn starch, silicone oil, a surfactant, and the like.

Plasticizers, compounds used to soften the microencapsulation material or film coatings to make them less brittle may also be included in the compositions. Examples of suitable plasticizers include, but are not limited to, polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

The compositions may further comprise solubilizers such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

In addition, the compositions my comprise stabilizers such as antioxidation agents, buffers, acids, preservatives and the like.

Suitable suspending agents for use in solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants including compounds such as sodium lauryl sulfate, sodium docusate, Tweens, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide and the like may also be included. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

Viscosity enhancing agents including, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof may also be included.

In addition, wetting agents including compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like may be included in these compositions.

In some embodiments, solid dosage forms, e.g., tablets, capsules, are prepared by mixing the egg yolk powder described herein, with one or more pharmaceutical excipients to form a bulk blend composition. When referring to these bulk blend compositions as homogeneous, it is meant that the particles of egg yolk powder are dispersed evenly throughout the composition so that the composition may be readily subdivided into equally effective unit dosage forms, such as tablets, pills, and capsules.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., "The Theory and Practice of Industrial Pharmacy" (1986).

It should be appreciated that there is considerable overlap between additives used in the solid dosage forms described herein. Thus, the above-listed additives should be taken as merely exemplary, and not limiting, of the types of additives that can be included.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials which sufficiently isolate the compound from other non-compatible excipients. Materials compatible with the egg yolk powder are those that delay the release of the egg yolk powder in vivo.

In other embodiments, the formulations described herein, which include the egg yolk powder, are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734.

In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components. The enteric coated oral dosage form may also be a capsule (coated or uncoated) containing pellets, beads or granules of the solid carrier or the composition.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating for the methods and compositions described herein to achieve delivery to the lower gastrointestinal tract.

In some embodiments, formulations are provided that include particles of egg yolk powder described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of egg yolk powder, the liquid dosage forms may include additives, such as: (a) disintegrating agents; (b) dispersing agents; (c) wetting agents; (d) at least one preservative, (e) viscosity enhancing agents, (t) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regards to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

In one nonlimiting embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the formulations described herein can be self-emulsifying drug delivery systems (SEDDS). Emulsions are dispersions of one immiscible phase in another, usually in the form of droplets. Generally, emulsions are created by vigorous mechanical dispersion.

SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563.

Buccal formulations that include egg yolk powder may be administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the egg yolk powder, and any other components that may be present in the buccal dosage unit. Generally, the polymeric carrier comprises hydrophilic (water-soluble and water-swellable) polymers that adhere to the wet surface of the buccal mucosa. Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

In certain embodiments, delivery systems for pharmaceutical compounds may be employed, such as, for example, liposomes and emulsions. In certain embodiments, compositions provided herein can also include a mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

The invention is further illustrated by the following example, which should not be construed as further limiting. The contents of all references, pending patent applications, and published patents cited throughout this application are hereby expressly incorporated by reference.

EXAMPLE

The egg yolk powder composition of FORTETROPIN when administered to aging dogs has been found to significantly improvement both mobility and activity of the aging dog in timeframes as short as one week.

More specifically, administration of FORTETROPIN for one month has been reported to increase leg strength allowing an aging dog to climb stairs and jump into automobiles without assistance. Administration of FORTETROPIN has also been reported to improve rear leg strength and decrease falling in aging dogs that had lost rear leg control thus causing frequent falls and slipping on hardwood floors. In addition, administration of FORTETROPIN was reported to decrease the occurrence of pulled muscles as evidenced by less limping following running and playing, to decrease stiffness following napping. Further, after administration of FORTETROPIN for three weeks, an aging dog was reported to exhibit more energy for walks and increased hind leg muscles.

What is claimed is:

1. A method for increasing mobility and activity in an aging dog, said method comprising administering orally to the aging dog on a daily basis a composition comprising fertilized egg yolk powder in an amount ranging from about 200-1000 mg/kg/day so that mobility and activity in the aging dog are increased as compared to prior to administering said composition.

2. The method of claim 1 wherein the dog has rheumatoid arthritis or osteoarthritis.

3. The method of claim 1 wherein the dog has hip dysplasia.

4. The method of claim 1 wherein the dog received long-term oral corticosteroid administration.

5. The method of claim 1 wherein the dog has a chronic disease associated with lean body mass wasting.

6. The method of claim 1 wherein the fertilized egg yolk derived product is FORTETROPIN.

7. The method of claim 1 wherein the composition comprises avian follistatin.

\* \* \* \* \*